(12) United States Patent
Kim

(10) Patent No.: US 7,985,309 B2
(45) Date of Patent: Jul. 26, 2011

(54) GAS GENERATING DEVICE AND USE OF THE DEVICE IN CONTINUOUS LIQUID SUPPLY

(75) Inventor: Yong-Nyun Kim, Seoul (KR)

(73) Assignee: E-WHA Fresenius Kabi Inc., Gyeonggi-do (KR)

( * ) Notice: Subject to any disclaimer, the term of this patent is extended or adjusted under 35 U.S.C. 154(b) by 2200 days.

(21) Appl. No.: 10/848,535

(22) Filed: May 17, 2004

(65) Prior Publication Data
US 2005/0006401 A1    Jan. 13, 2005

Related U.S. Application Data

(63) Continuation of application No. PCT/KR02/02140, filed on Nov. 15, 2002.

(51) Int. Cl.
*C06B 45/18* (2006.01)
*C06B 45/30* (2006.01)
*D03D 23/00* (2006.01)
*D03D 43/00* (2006.01)

(52) U.S. Cl. ............ 149/3; 149/5; 149/109.4; 149/109.6
(58) Field of Classification Search .................. 149/3, 5, 149/109.4, 109.6
See application file for complete search history.

(56) References Cited

U.S. PATENT DOCUMENTS

| | | |
|---|---|---|
| 4,744,442 A | 5/1988 | Bras et al. |
| 4,813,937 A | 3/1989 | Vaillancourt |
| 4,847,093 A | 7/1989 | Ayer et al. |
| 5,312,389 A | 5/1994 | Theeuwes et al. |
| 5,397,303 A | 3/1995 | Sancoff et al. |
| 5,398,850 A * | 3/1995 | Sancoff et al. ............. 222/386.5 |
| 5,398,851 A | 3/1995 | Sancoff et al. |
| 5,522,526 A | 6/1996 | DeLaforcade et al. |
| 5,553,741 A | 9/1996 | Sancoff et al. |
| 5,558,255 A | 9/1996 | Sancoff et al. |
| 5,571,261 A | 11/1996 | Sancoff et al. |
| 5,578,005 A | 11/1996 | Sancoff et al. |

(Continued)

FOREIGN PATENT DOCUMENTS

JP    50-109195    8/1975

(Continued)

OTHER PUBLICATIONS

Schmidt, Peter C., et al., << Effervescent tablets. Which acidic components are the most suitable ?>> In *Deutsche Apotheker Zeitung*, 1987, 127 (19), pp. 991-997.

(Continued)

*Primary Examiner* — James E McDonough
(74) *Attorney, Agent, or Firm* — Sughrue Mion, PLLC

(57) ABSTRACT

The present invention relates to a solid formulation, more particularly to a pellet-type formulation that produces $CO_2$ gas in a constant rate when contacting liquid acid. The pellet-type formulation of the invention is characterized in that the pellet is produced by the following: preparing a pellet by extrusion molding a composition that comprises a major amount of Sodium Carbonate ($Na_2CO_3$) and a minor amount of gelatin, and additionally a minor amount of synthetic resin that hardly reacts with acid; coating said pellet with a resin that hardly reacts with acid; and forming a recess or a hole at the center of the pellet. The present invention also relates to a process of preparing a pellet-type formulation that produces $CO_2$ gas in a constant rate when contacting liquid acid.

17 Claims, 1 Drawing Sheet

U.S. PATENT DOCUMENTS

| | | | |
|---|---|---|---|
| 5,588,556 | A | 12/1996 | Sancoff et al. |
| 5,700,245 | A | 12/1997 | Sancoff et al. |
| 5,766,147 | A | 6/1998 | Sancoff et al. |
| 5,992,700 | A | 11/1999 | McGlothlin et al. |
| 6,786,365 | B2 | 9/2004 | Kim |
| 2003/0168480 | A1 * | 9/2003 | Kim .............................. 222/399 |
| 2005/0209562 | A1 | 9/2005 | Kim |

FOREIGN PATENT DOCUMENTS

| | | |
|---|---|---|
| JP | 02-102664 | 4/1990 |
| JP | 04-312469 | 11/1992 |
| KR | 98-24858 | 7/1998 |
| KR | 20-150725 | 4/1999 |
| KR | 10-0262930 | 5/2000 |
| KR | 20-205619 | 9/2000 |
| KR | 10-2001-0039742 A | 5/2001 |
| WO | WO 99/04765 | 2/1999 |
| WO | 02/11791 A1 | 2/2002 |
| WO | 03/066138 | 8/2003 |

OTHER PUBLICATIONS

European Search Report dated Mar. 18, 2010 in counterpart European Application No. 09151501.5.

* cited by examiner

GAS GENERATING DEVICE AND USE OF THE DEVICE IN CONTINUOUS LIQUID SUPPLY

RELATED APPLICATIONS

This application claims for the benefit of and is a continuation of International Application No. PCT/KR02/02140 filed Nov. 15, 2002, designating the United States and claiming for the benefit of the earlier filing dates under 35 U.S.C. §365 (b) of Korean Patent Application No. 2001/71529 filed Nov. 16, 2001, which is hereby incorporated herein by reference in its entirety. International Application No. PCT/KR02/02140 was published in English as WO 03/04191 A1 on May 22, 2003, and is hereby incorporated herein by reference in its entirety.

TECHNICAL FIELD

The present invention relates to a solid formulation for use in generating a gas and various uses of the formulation and an apparatus using the formulation

BACKGROUND ART

Korean Patent Application Nos. 2000-63790 and 2000-42128, International Application No. PCT/KR00/01530 and its International Publication No. WO 02/11791 A1, all of which are incorporated herein by reference in their entirety, disclose a portable liquid supply apparatus for continuously injecting medicine into a patient in a constant quantity per unit time and over a long period of time for the purpose of curing of a specific disease. In order to continuously inject a medicine in a constant quantity per unit time and over a long period of time, the patient should be in a hospital or stay at home. This is economically and physically inconvenient for the patient and his/her family. Therefore, the aforementioned patent applications disclose an improved portable liquid supply apparatus capable of injecting the medicine in a constant rate in order to eliminate such inconvenience and cure the patient over a long period of time.

In such a liquid supply apparatus, it is important to continuously inject the medicine in a constant quantity per unit time for a predetermined period of time. The liquid supply apparatuses disclosed and proposed in the patent applications are apparatuses for injecting medicine at a constant rate, wherein a piston is pushed by means of mechanical drive or by an action of gas produced at a constant rate.

A device for pushing the piston by the production of gas is a device constructed to cause solid and liquid materials, which are separately stored, to come into contact and react with each other so that the gas is produced therefrom. Particularly, the solid material consists of sodium bicarbonate ($NaHCO_3$) and KBr; or sodium bicarbonate, gelatin and a small amount of Talc. The liquid material consists of an L-tartaric acid ($C_4H_6O_6$) solution. They are caused to react with each other to produce $CO_2$ gas of which produced gas pressure in turn pushes the piston.

However, it is not easy to consistently maintain an initial amount of gas, i.e. $CO_2$ gas produced by means of the reaction between the solid and liquid materials, and to consistently control and maintain a production rate of the gas thereafter, which are disclosed in the patent applications.

SUMMARY OF THE INVENTION

One aspect of the present invention provides a gas generating device, which comprises: a body formed from a composition comprising a chemical compound which is capable of generating a gas from a reaction of the composition with an activating compound; a coating of a material on the body, the material being substantially resistant to the activating compound; and at least one exposed area of the body that is not covered by the coating.

In the above-described device, the composition may further comprise gelatin. The gelatin may be contained in the composition in an amount sufficient to maintain a structure of the body by absorbing at least a portion of the water generated along with the gas during the reaction. The gelatin may be contained in an amount from about 0.5% to about 5% of a total weight of the composition. The gelatin may be contained in an amount from about 1.5% to about 3% of a total weight of the composition. The composition may further comprise a resin substantially resistant to the activating compound. The resin may be contained in the composition in an amount sufficient to sustain the reaction between the chemical compound and the activating compound for an extended period of time. The resin may be contained in an amount from about 3% to about 15% of a total weight of the composition. The resin may be contained in an amount from about 5% to about 10% of a total weight of the composition. The chemical compound may be contained in the composition in an amount from about 70% to about 95% of a total weight of the composition. The composition may comprise from about 87 wt % to about 92 wt % of the chemical compound, from about 5% to about 10% of PMMA resin, and from about 1.5% to about 3% of gelatin.

In the above-described device, the exposed area may be substantially smaller than the total surface area of the body. Prior to the reaction with the activating compound, the exposed area may be less than about 20% of the total surface area of the body. The body may have a substantially cylindrical hollow or aperture, wherein the at least one exposed area may be located on a surface of the substantially cylindrical hollow. The body may be substantially cylindrical and may have a substantially cylindrical hollow. The at least one exposed area may be located on a surface of the substantially cylindrical hollow. The body may be substantially elongated. The at least one exposed area may be located at about an end of the substantially elongated body. The chemical compound may be selected from the group consisting of metal carbonates and metal hydrogen carbonates. The metal carbonates comprise sodium carbonate, potassium carbonate, calcium carbonate and magnesium carbonate, and the metal hydrogen carbonates comprise sodium hydrogen carbonate and potassium hydrogen carbonate. The activating compound may be selected from the group consisting of tartaric acid, citric acid, acetic acid, oxalic acid, lactic acid, succinic acid, malic acid, maleic acid, fumaric acid, hydrochloric acid and sulfuric acid.

Another aspect of the present invention provides a method of making the above-described device. The method comprises: providing the composition comprising the chemical compound; forming the composition into a shaped body; coating the shaped body of the composition with a material substantially resistant to the activating compound; and forming the at least one exposed area. The method may further comprise designing shape, size and location of the at least one exposed area so as to accomplish a controlled generation of the gas for an extended period of time upon contacting the device with the activating compound. The extended period of time may be from about 3 minutes to about 24 hours.

Another aspect of the present invention provides a method of generating a gas. The method comprises: providing the above-described device; contacting the device with the activating compound; and allowing the activating compound to contact the at least one exposed area of the device and to react with the chemical compound of the composition, thereby generating the gas.

Another aspect of the present invention provides a method of moving a piston. The method comprises: contacting the activating compound with the chemical compound through the at least one exposed area of the above-described device, thereby generating a gas; collecting the generated gas in an enclosed space, the gas having a pressure within the enclosed space; and moving a piston with the pressure of the gas.

Still another aspect of the present invention provides a method of supplying a liquid. The method comprises: providing a liquid contained in a container having an outlet; providing the above-described device and the activating compound; contacting the activating compound with the chemical compound through the at least one exposed area of the device, thereby generating a gas; collecting the generated gas in an enclosed space, the gas having a pressure within the enclosed space; forcing the liquid contained in the container with the pressure of the gas, thereby discharging the liquid from the container through the outlet; supplying the discharged liquid to a person or object in need of such supply. In this method, contacting the activating compound with the chemical compound may be continued for an extended period of time. Supplying the discharged liquid may be continued for an extended period of time.

Still another aspect of the present invention provides a liquid supplying apparatus. The apparatus comprises: a holder configured to hold the above-described device; the activating compound; an activator configured so that the device and the activating compound are in contact with each other so as to generate a gas; and a liquid container for containing a liquid, the liquid container having an interior volume, wherein the interior volume of the liquid container may be configured to be susceptible to an amount of the generated gas such that the interior volume decreases substantially proportionally to an amount of the generated gas.

A still further aspect of the present invention provides a solid composition for use in generating a gas. The composition comprises gelatin and a chemical compound capable of generating a gas in a reaction with an acid. The gelatin may be contained in an amount from about 1.5% to about 3% of a total weight of the composition. The composition may further comprise a resin substantially resistant to the acid.

Another aspect of the present invention is to provide a new $CO_2$ gas-producing solid formulation capable of producing $CO_2$ gas at a constant rate for a predetermined period of time through a reaction with an acid.

Another aspect of the present invention is to provide a solid formulation prepared in the form of a pellet with a recess or hole at the center thereof so as to produce $CO_2$ gas at a constant rate for a predetermined period of time.

A further aspect of the present invention is to provide a process of preparing the pellet-type formulation.

A still further aspect of the present invention is to provide a process of producing $CO_2$ gas at a constant rate for a predetermined period of time by causing the pellet-type formulation prepared according to the present invention to react with a liquid acid.

An embodiment of the present invention provides a pellet-type formulation capable of producing $CO_2$ gas at a constant rate when coming into contact with a liquid organic acid and a process of preparing the pellet-type formulation, wherein the pellet-type formulation is produced by preparing a pellet through extrusion molding of a composition comprising a major amount of sodium carbonate ($Na_2CO_3$), a minor amount of gelatin and an additional minor amount of synthetic resin that hardly reacts with the acid, coating the pellet with a resin that hardly reacts with the acid, and forming a hole at the center of the coated pellet.

A pellet-type formulation is capable of producing $CO_2$ gas at a constant ratio when coming into contact with an acid, which is produced by preparing a pellet through extrusion molding of a composition comprising a major amount of sodium carbonate ($Na_2CO_3$) and a minor amount of gelatin, coating the pellet one or more times with a resin solution that hardly reacts with the acid, and forming a recess or hole at the center of the coated pellet.

In the pellet-type formulation, the sodium carbonate ($Na_2CO_3$) as a main component of the composition constituting the pellet is a substance that reacts with an acid and produces the $CO_2$ gas. For example, a reaction between the sodium carbonate and citric acid as the acid for producing the $CO_2$ gas can be expressed as the following chemical formula:

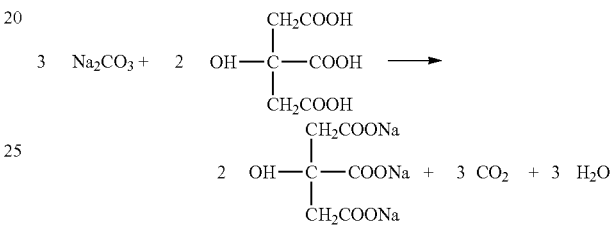

The sodium carbonate is preferably prepared by mixing light ash and heavy ash with 99.2% or more purity for food additives at a ratio of 50:50. Light ash and heavy ash for different uses other than food additives may also be used to produce $CO_2$ gas through the reaction with the acid. However, it is preferred that the light ash and heavy ash for food additives be used in view of safety since they are employed in a gas producing device for use in a portable liquid supply apparatus for injecting medicine into a patient for a predetermined period of time in the same manner as a preferred example of the present invention. Using the mixture of light ash and heavy ash as the sodium carbonate is to facilitate mixture thereof with the gelatin that is another component of the solid formulation. Since particles of the gelatin are large, a uniform mixture may not be achieved if sodium carbonate comprising only light ash is used.

In the pellet-type formulation, the gelatin has a property by which when coming into contact with moisture, it absorbs the moisture and swells. Therefore, in a process where the pellet reacts with the acid to produce $CO_2$ gas, the gelatin absorbs moisture constituting the acid and swells within the pellet. The swollen gelatin fills space that was occupied by the sodium carbonate within the pellet and has reacted with acid to produce $CO_2$ gas and has been dissolved away. Owing to the action of the gelatin, the contact area of the sodium carbonate within the pellet with the acid can be maintained at a substantially constant level even when the size of the gas-producing hole formed in the pellet is gradually increased as the reaction continuously proceeds. Thus, even though the reaction continuously proceeds for a predetermined period of time, the amount of $CO_2$ gas produced per unit time can be kept constant. The present inventor found that the gelatin is a desirable substance for performing such an action. However, the present invention is not limited thereto. It will be readily understood by those skilled in the art that if there are different kinds of excipients having properties by which they absorb moisture and swell but do not react with an acid or other substances constituting the pellet in the same manner as the gelatin, the excipients may be used as components constituting the pellet according to the present invention for achieving the same object as the gelatin.

As for the gelatin, gelatin with a particle size of 30 mesh or less, preferably 50 to 100 mesh is used. If the particle size of the gelatin is larger than the above range, the gelatin may swell excessively and hinder contact of the sodium carbonate with the acid, which is required for the production of an amount of $CO_2$ gas above a predetermined level. Therefore, since there is a difficulty in smoothly producing $CO_2$ gas, an amount of $CO_2$ gas less than a desired amount per unit time may be produced. On the contrary, if the particle size of the gelatin is smaller than the above range, the gelatin that has absorbed the moisture and thus swelled cannot properly fill the empty space within the pellet. Accordingly, since the contact area of the sodium carbonate with the acid may be gradually increased, the amount of $CO_2$ gas produced per unit time may also be gradually increased.

The pellet composition for preparing the pellet formulation preferably comprises 450 to 550 parts by weight of heavy ash, 450 to 550 parts by weight of light ash, and 10 to 40 parts by weight of gelatin. More particularly, it comprises 500 parts by weight of heavy ash, 500 parts by weight of light ash, and 20 to 30 parts by weight of gelatin.

If the amount of gelatin is larger than the above range, the gelatin swells excessively as the pellet reacts with the acid, and thus, it may hinder the sodium carbonate within the pellet from reacting with the acid. On the contrary, if the amount of gelatin is less than the above range, the gelatin within the pellet is dissolved and flows out as the pellet reacts with the acid, and thus, the pellet cannot maintain its proper shape. Accordingly, since the sodium carbonate rapidly reacts with the acid, a constant amount of gas per unit time cannot be produced. Further, if the amount of gelatin is very large, it may be difficult to uniformly mix the gelatin with the other components.

Adjustment of the composition ratios of the heavy ash, light ash and gelatin within the ranges of the ratios can control the amount of $CO_2$ gas produced per unit time when they come into contact with the acid. That is, if the amounts of the heavy ash and light ash are increased within the above ranges thereof with a fixed amount of gelatin, the amount of the $CO_2$ gas produced per unit time may be increased. On the contrary, if the composition ratio of the gelatin is increased while the amounts of heavy ash and light ash remain fixed, the amount of the $CO_2$ gas produced per unit time may be decreased.

The components can be used by properly mixing them in the form of powder. The components can be easily mixed with one another by using various methods known in the art. Particularly, they are conveniently mixed by properly stirring them using a V-mixer or the like for about 5 minutes to 1 hour, preferably about 10 to 30 minutes.

The acid capable of producing $CO_2$ gas through the reaction with the pellet-type formulation composed of the above components may include any kind of acid. However, the acid is preferably an organic acid such as L-tartaric acid or citric acid in order to use it in such a portable liquid supply apparatus for injecting medicine into a human body as described above. However, the acid for use in the pellet formulation of the present invention is not limited thereto.

The pellet is produced by mixing the above components at the preferred ratios described above and by extrusion molding the mixture thereof. The extrusion molding can be performed by known methods using molding machines well known to those skilled in the art in order to mold the pellet formulation. Preferably, the extrusion molding is performed by molding the mixture for about 5 to 10 seconds, preferably about 8 seconds, and by extruding it for about 3 seconds, using a molding machine with a power capacity of 15 Tons (125 kg/cm$^2$) in a temperature range of about 100 to 150□.

Although the pellet produced by the extrusion molding in such a way generally takes the shape of a cylinder, it is preferred that top and bottom surfaces or one surface of the pellet be smoothly curved in the form of a dome. This is to prevent breakage of the pellet when a recess or hole is subsequently formed in the pellet. However, the shape of the pellet is not limited to the cylindrical shape. Those skilled in the art can properly modify and adjust the size and shape of the pellet according to a desired amount of $CO_2$ gas produced per unit time.

In order to prepare the pellet-type formulation of the present invention, the pellet produced as such is then coated with a resin solution that hardly reacts with the acid. The resin that hardly reacts with the acid includes polymethyl methacrylate (PMMA) resin, polyvinyl acetate (PVAC; condensate of vinyl chloride and vinyl acetate) resin, and polystyrene (PS) resin that is particularly suitable for a predetermined time delay until the pellet produces $CO_2$ gas by delaying the initial reaction time even though the pellet reacts with the acid. In addition, as for resins that hardly react with the acid or delays the time for reaction with the acid, there have been known polyurethane-based resin, silicon-based resin, modified silicon-based resin, polysulfide-based resin, acrylic emulsion-based resin, and the like. However, the present invention is not limited thereto. Those skilled in the art can select and use a proper kind of resin according to the purpose and effect thereof.

These resins are solid resins and thus can be used after being dissolved at predetermined concentrations in proper solvents for use. Although toluene may be employed as a proper solvent, the present invention is not limited thereto.

The resin is dissolved in a proper solvent, and then, the pellet is immersed in the resin solution or the resin solution is sprayed onto the pellet so that the pellet can be coated with the resin solution. In order to cause the pellet-type formulation to produce $CO_2$ gas at a constant rate, it is preferred that the coating be performed one or more times, by repeating the coating and drying steps. In case of coating the pellet one or more times, the same kind of resin solution or different kinds of resin solutions may be used for each coating step. The drying of the resin solution can be performed within a low temperature dryer or the like for a predetermined period of time.

The recess or hole for production of $CO_2$ gas is formed in the coated pellet. The recess or recesses may be formed on only one side or both sides of the pellet with respect to the center of the pellet. The hole may be formed at once through the pellet from the top to the bottom of the pellet. However, in order to easily release the pellet from the molding machine upon extrusion molding of the pellet, it is preferred that a protrusion be generally formed at the center of a bottom surface of the molding machine so that the molded pellet can be formed beforehand with a depression extending from the center of the bottom of the pellet to a predetermined position within the pellet. Therefore, in the case where the depression is formed in the pellet, the pellet is drilled from the top thereof to a ceiling portion of the previously formed depression so as to form the hole through the center of the pellet. Alternatively, the pellet may be drilled downward from the top thereof only to the extent that the drilled recess does not come into contact with the ceiling portion of the depression, thereby forming the recess.

Although it is preferred that the size of the recess or hole be formed to be about 1/20 to 1/3 times as large as a diameter of the pellet, it is not limited thereto. It can be understood by those skilled in the art that the size and shape of the recess or hole can be easily adjusted according to a desired amount of $CO_2$ gas to be produced per unit time. In the case where the depression is beforehand formed at the bottom of the pellet, the depression is generally formed such that its diameter decreases from the bottom to the top of the pellet. At this time, it is preferred that the hole drilled from the top of the pellet have a diameter similar to that of the ceiling portion of the depression.

Further, in the case where the depression is beforehand formed at the bottom of the pellet when molding the pellet, since the pellet is coated with the resin solution that hardly reacts with the acid, and the pellet is drilled from the top thereof to form the recess or hole, an inner wall surface for defining the previously formed depression is in a state where it has been coated with the coating solution that hardly reacts with the acid, and an inner wall surface of the recess or upper hole portion that has been formed after the coating is not coated with the coating solution. Therefore, the inner wall surface of the recess or upper hole portion formed from the top of the pellet produces $CO_2$ gas when coming into contact with the acid, whereas the inner wall surface of the depression formed from the bottom of the pellet hardly reacts with the acid not to produce $CO_2$ gas and merely serves as a passage through which the $CO_2$ gas produced mainly from the upper hole portion flows. By forming the recess or hole in such a way, the amount of $CO_2$ gas to be produced can be controlled and a smooth flow of the $CO_2$ gas can be established. Further, it can be understood that the amount of $CO_2$ gas produced per unit time can also be controlled by adjusting the height of the previously formed depression and the size of the recess or upper hole portion.

According to a second aspect of the present invention, there is provided a pellet-type formulation capable of producing $CO_2$ gas at a constant rate when coming into contact with an acid, which is produced by preparing a pellet through extrusion molding of a composition comprising a major amount of sodium carbonate ($Na_2CO_3$) and minor amounts of gelatin and a resin that hardly reacts with the acid, coating the pellet one or more times with a resin solution that hardly reacts with the acid, and forming a recess or hole at the center of the coated pellet.

As for composition ratios of the components of the pellet composition for preparing the pellet-type formulation, the composition preferably comprises 450 to 550 parts by weight of light ash and 450 to 550 parts by weight of heavy ash, which constitute the sodium carbonate, 10 to 40 parts by weight of gelatin, and 50 to 120 parts by weight of resin that hardly reacts with the acid. More preferably, the composition comprises 500 parts by weight of light ash and 500 parts by weight of heavy ash, 20 to 30 parts by weight of gelatin, and 60 to 100 parts by weight of resin that hardly reacts with the acid.

The pellet-type formulation according to the second aspect of the present invention is different from the pellet-type formulation according to the first aspect of the present invention in that the composition constituting the pellet further comprises the resin that hardly reacts with the acid in addition to the sodium carbonate and the gelatin. As described above, the resin that hardly reacts with the acid includes polymethyl methacrylate (PMMA) resin, polyvinyl acetate (PVAC; condensate of vinyl chloride and vinyl acetate) resin, and polystyrene (PS) resin, polyurethane-based resin, silicon-based resin, modified silicon-based resin, polysulfide-based resin, acrylic emulsion-based resin, and the like. Although the resin is preferably PMMA resin, the present invention is not limited thereto.

Adjustment of the composition ratios of the heavy ash, light ash, gelatin and resin that hardly reacts with the acid within the ranges of the ratios can control the amount of $CO_2$ gas produced per unit time when they come into contact with the acid. That is, if the amounts of heavy ash and light ash are increased within the above ranges thereof while the amounts of gelatin and resin that hardly reacts with the acid remain fixed, the amount of $CO_2$ gas produced per unit time may be increased. On the contrary, if the composition ratios of the gelatin and resin that hardly reacts with the acid are increased while the amounts of heavy ash and light ash remain fixed, the amount of $CO_2$ gas produced per unit time may be decreased.

There are generally two methods of mixing the resin, which hardly reacts with the acid, with the other components constituting the pellet. The first method is to directly mix the resin in the form of powder with the other components and to extrusion mold the mixture thereof. The second method is to dissolve the resin in a proper solvent, e.g., toluene, to obtain a solution and to mix the solution with the other components of the pellet, i.e. a mixture of the sodium carbonate and gelatin in the form of powder. Either one of the methods may be properly employed. A method of properly mixing the above components and producing the pellet is the same as the first aspect of the present invention. That is, the method is conveniently performed by mixing the components using a mixer such as a V-mixer for a proper period of time, e.g., about 1 minute to 1 hour, preferably about 10 to 30 minutes.

In the case where the resin is mixed in the form of a solution, the remaining components, i.e. the light ash, heavy ash and gelatin, are charged into the V-mixer and mixed with one another for about 30 minutes. Then, the resin solution obtained by dissolving the resin in a proper solvent is added thereto and they are further mixed with each other by again using the V-mixer for about 30 minutes. After mixing for the predetermined period of time, the mixture is put at room temperature for a predetermined period of time so that the solvent can be volatilized therefrom. After the volatilization of the solvent, it is preferred that the mixture be mixed once more by using the V-mixer for about 10 to 20 minutes.

In the case where the resin is mixed in the form of powder as it is, the heavy ash, light ash, gelatin and resin powder can be mixed with one another within the V-mixer or the like for a predetermined period of time. More preferably, the light ash and resin powder that are small in particle size are first mixed with each other and then the heavy ash and gelatin are added thereto. In such a case, it is possible to obtain a more uniformly mixed mixture thereof.

After the uniform mixing of the components constituting the pellet in such a way, the pellet is produced by extrusion molding the mixture in the same manner as the first aspect of the present invention described above. After the production of the pellet, as described above in connection with the first aspect of the present invention, the produced pellet is coated with a resin that hardly reacts with the acid. A subsequent process of forming a recess or hole in the coated pellet by using a drill or the like proceeds to produce the pellet-type formulation according to the present invention.

Further, in the case where the resin is mixed in the form of powder, it is preferred that the pellet obtained after molding thereof be put at a temperature of about 200 to 250□ to which room temperature is increased by using a high temperature dryer or the like, for 10 minutes to 1 hour, preferably 20 to 50 minutes. The reason is that the present inventor believes experientially rather than theoretically that the resin component included in the pellet would be melted and come into close contact with the heavy ash and light ash so as to consistently maintain the amount of $CO_2$ gas produced per unit time by delaying the production of $CO_2$ gas when the pellet reacts with the acid.

The kinds of resins for coating the pellet, which hardly react with the acid, methods of forming the recess or hole in the pellet, and the like are the same as the first aspect of the present invention.

Meanwhile, it is preferred that in the pellet-type formations according to the first and second aspects of the present invention, a side surface of the pellet be completely wrapped with a shrinkable film. The shrinkable film preferably wraps the entire side surface of the pellet and marginal portions including edges of the top and bottom surfaces of the pellet, or only the edges of the top and bottom surfaces of the pellet. The shrinkable film prevents the edges of the pellet from being broken. Thus, it can prevent the acid from permeating cracks in the broken edges of the pellet. The shrinkable film is preferably a PVC film. After the pellet is wrapped with the shrinkable film, the film is dried using a hot air dryer to be shrunk.

An embodiment of the present invention provides a process of preparing the pellet-type formulation.

That is, there is provided a process of preparing the pellet-type formulation capable of producing $CO_2$ gas when coming into contact with an acid, comprising the steps of: preparing a pellet composition by mixing a major amount of sodium carbonate ($Na_2CO_3$), a minor amount of gelatin and an additional minor amount of resin that hardly reacts with the acid; producing a pellet through extrusion molding of the composition; coating the pellet with a resin solution, which hardly reacts with the acid, one or more times and drying the coated pellet; and forming a recess or hole at the center of the coated pellet.

In the process of preparing the pellet-type formulation, the pellet composition preferably comprises the sodium carbonate comprising light ash and heavy ash with 99.2% or more purity for food additives at a ratio of 50:50, the gelatin with a particle size of 30 mesh or less, and the additional resin that hardly reacts with the acid. More preferably, in a case where the composition comprises the sodium carbonate and the gelatin, it can comprises 450 to 550 parts by weight of light ash and 450 to 550 parts by weight of heavy ash, and 10 to 40 parts by weight of gelatin. In a case where the composition further comprises the additional resin that hardly reacts with the acid, 50 to 120 parts by weight of resin can be added thereto. More particularly, the composition comprises 500 parts by weight of light ash and 500 parts by weight of heavy ash, 20 to 30 parts by weight of gelatin, and 60 to 100 parts by weight of resin that hardly reacts with the acid. The particle size of the gelatin is preferably in a range of 50 to 100 mesh, more particularly, 80 to 100 mesh. As for the resin that hardly reacts with the acid, PMMA resin, PVAC resin, PS resin, polyurethane-based resin, silicon-based resin, modified silicon-based resin, polysulfide-based resin, acrylic emulsion-based resin, and the like can be used. However, the present invention is not limited thereto.

The composition can be prepared by properly mixing the components. The mixing can be made by charging the components into a mixer well known in the art, such as a V-mixer, and mixing them therein for a predetermined period of time. There are two methods of mixing the resin, which hardly reacts with the acid, with the other components: a method of mixing the resin in the form of powder with the other components, and a method of mixing beforehand the other components in the form of powder with one another and adding the resin component, which has been made in the form of a solution, thereto. Even at this time, a mixer such as a V-mixer can be used. The mixing methods are the same as described above.

The conditions of extrusion molding the composition can be established according to known methods using molding machines well known to those skilled in the art. Preferably, the extrusion molding is performed by molding the mixture for about 5 to 10 seconds, preferably about 8 seconds, and by extruding it for about 3 seconds, using a molding machine with a power capacity of 15 Tons (125 kg/cm$^2$) in a temperature range of about 100 to 150□.

Although the pellet produced by the extrusion molding in such a way generally takes the shape of a cylinder, it is preferred that top and bottom surfaces of the pellet be smoothly curved in the form of a dome. However, those skilled in the art can properly modify and adjust the size and shape of the pellet according to a desired amount of $CO_2$ gas produced per unit time.

In order to prepare the pellet-type formulation according to an embodiment of the present invention, the pellet produced in such a way should be coated with the resin solution that hardly reacts with the acid. Before the coating, it is preferred that raw material powder adhering to an outer surface of the pellet should be blown away by air so that the pellet can be cleaned.

The kind of resin for the coating that hardly reacts with the acid is the same as the additional resin component of the composition. One, or two or more resins may be selected and the pellet may then be coated one, or two or more times. Since the resins are in a solid state, they are dissolved in proper solvents such as toluene to obtain solutions with predetermined concentrations, e.g. 10% to 60%, which in turn are coated on the pellet. The coating of the pellet can be made by dissolving the resins in the solvents and spraying the solutions, or by immersing the pellet in the resin solutions for predetermined periods of time. The coating is preferably made by repeating the coating and drying steps one or more times, more preferably two or more times, further more preferably three or more times.

In case of performing the coating by immersing the pellet in the resin solutions, the pellet is immersed in the resin solutions to be coated for about 1 minute to several hours, preferably about 5 minutes to 1 hour. In case of performing the spray coating, the resin solutions are prepared at such concentrations that the resin solutions cannot flow down, and then are uniformly sprayed and coated onto a plurality of pellets which have been contained in a jig or the like.

The drying of the pellet after the coating is performed by putting it in the low temperature dryer or the like for a predetermined period of time. The drying is performed at a temperature of the low temperature dryer of about 60 to 90□, preferably about 70 to 80□ for a proper period of time in a range of 10 minutes to 12 hours in accordance with the degree of coating.

On the other hand, in a case where the pellet composition comprises the resin that hardly reacts with the acid and the pellet is produced by mixing the resin in the form of powder with the other components of the composition and extrusion molding the mixture, as described above, it is preferred that the pellet obtained after molding thereof be put at a temperature about 200 to 250□ to which room temperature is increased by using the high temperature dryer or the like, for 10 minutes to 1 hour, preferably 20 to 50 minutes. Subsequently, the pellet is preferably cooled down and then coated.

In case of coating the pellet one or more times, the same kind of resin solution or different kinds of resin solutions may be used for each coating step. In this case, those skilled in the art can properly control the concentration of the coating solution, the coating time, the drying time and the like in accordance with the kind of the coating resin.

The recess or hole for production of $CO_2$ gas is formed in the coated pellet. The hole may be formed at once through the pellet from the top to the bottom of the pellet. Alternatively, as described above, in the case where the protrusion is formed at the center of the bottom surface of the molding machine in order to easily release the pellet from the molding machine upon extrusion molding of the pellet, the pellet may be drilled from the top thereof only to the ceiling portion of the previously formed depression in the pellet so as to form the hole through the center of the pellet.

Although it is preferred that the size of the recess or hole be formed to be about 1/20 to 1/3 times as large as the diameter of the pellet, it is not limited thereto. The size or depth of the recess or hole can be easily adjusted according to a desired amount of $CO_2$ gas to be produced per unit time. In the case where the depression is beforehand formed at the bottom of the pellet, the depression is generally formed such that its diameter decreases from the bottom to the top of the pellet. At this time, it is preferred that the hole drilled from the top of the pellet have a diameter similar to that of the ceiling portion of the depression.

As described above, in the case where the depression is beforehand formed at the bottom of the pellet when molding the pellet, since the inner wall surface for defining the depression has been coated with the coating solution that hardly reacts with the acid, the inner wall surface of the depression hardly produces $CO_2$ gas when coming into contact with the acid. Therefore, the inner wall surface of the depression merely serves as the passage through which the $CO_2$ gas produced from the upper hole portion of the pellet flows. Since the wall surface for defining the upper hole portion of the pellet, which is formed after the coating of the pellet, is not coated with the coating solution, it serves to produce $CO_2$ gas through the reaction with the acid.

Meanwhile, the preparation method may further comprise the step of additionally coating the pellet with a coating solution, which delays the reaction with the acid, one or more times after forming the recess or hole. The additional coating is made by slightly coating the pellet-type formulation, which has been formed with the hole, with PS resin for delaying the reaction with the acid. The coating may be made by immersing the pellet in the coating solution for a short period of time or spray coating it thinly. With such coating, the upper inner wall surface of the recess or hole is also coated with the coating solution capable of delaying the reaction with the acid. According to such a constitution, even in the case where the pellet-type formulation once comes into contact with the acid, $CO_2$ gas will be produced in the recess or hole only after considerable time passes. In a case where the pellet-type formulation according to an embodiment of the present invention is used in a device for pushing a piston by means of produced $CO_2$ gas in a portable injector or the like, this can prevent $CO_2$ gas from rapidly being produced as soon as the pellet comes into contact with the acid, in consideration that the piston is pushed according to a change in pressure within the piston itself produced in a process of bringing the pellet-type formulation into contact with an acid solution. Therefore, according to an embodiment of the present invention, there is provided a method of preparing the pellet-type formulation wherein $CO_2$ gas can be gradually produced only after a predetermined period of time passes. As can be seen from the above constitution, since the third coating solution is not a solution that never reacts with the acid, $CO_2$ gas is produced through the contact with the acid in the hole after the predetermined period of time passes, contrary to the other portions of the pellet coated with the coating solution that hardly reacts with the acid.

Moreover, the method of preparing the pellet-type formulation may further comprise the step of completely wrapping the side surface of the pellet with a shrinkable film after the pellet is molded and primarily coated. The shrinkable film preferably wraps the entire side surface of the pellet and the marginal portions including the edges of the top and bottom surfaces of the pellet. Alternatively, only the edges of the top and bottom surfaces of the pellet may be wrapped with the shrinkable film. The shrinkable film prevents the edges of the pellet from being broken. Thus, it can prevent the acid from permeating cracks in broken edges of the pellet.

BRIEF DESCRIPTION OF THE DRAWINGS

Non-exclusive examples of the present invention will be described with reference to the accompanying drawings, in which.

DETAILED DESCRIPTION OF THE EMBODIMENTS

Hereinafter, preferred examples of a pellet-type formulation will be described with reference to the accompanying drawings, and then, a preparation example of the pellet-type formulation will be explained. The examples do not limit the present invention but are only for illustrative purposes.

Figure 1:
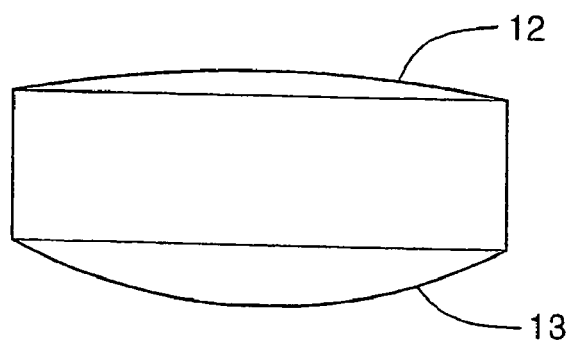
FIG. 1 is a side view of a pellet of a pellet-type formulation prepared according to an example of the present invention.
Figure 2:
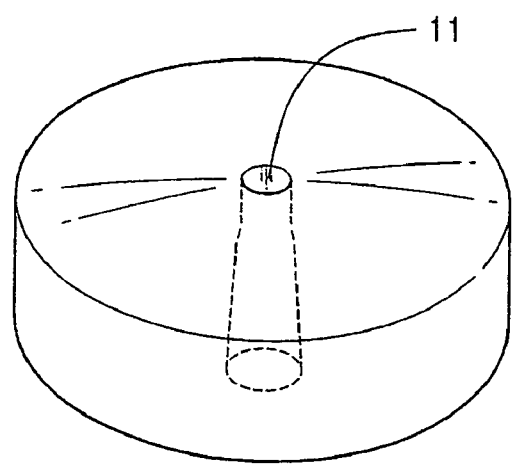
FIG. 2 is a schematic perspective view of the pellet-type formulation.
Figure 3:
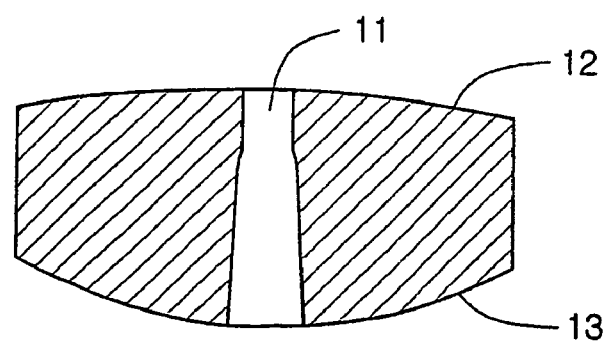
FIG. 3 is a longitudinal sectional view of the pellet-type formulation shown in FIG. 1.

FIG. 1 is a schematic perspective view of the pellet-type formulation, and FIG. 2 is a longitudinal sectional view of FIG. 1.

As shown in FIG. 1, although the pellet-type formulation generally takes the shape of a cylinder in the same manner as a general pellet, top and bottom surfaces 12, 13 of the pellet are smoothly curved. If the top and bottom surfaces of the pellet are curved in such a way, edges of the top and bottom surfaces of the pellet can be prevented from being broken when forming a hole 11 at the center of the pellet. The center of the pellet is formed with the hole 11. The size of the hole can be properly adjusted to have a diameter that is about 1/20 to 1/3 times as large as the diameter of the pellet.

Hereinafter, examples of the preparation of the pellet-type formulation will be described.

Example 1

Preparation of Pellet-Type Formulation

Pellets in the form of a cylinder with a diameter of about 20 mm and a height of about 5 mm were produced by charging 3000 g of light ash and 3000 g of heavy ash with 99.2% or more purity for food additives and 180 g of gelatin with a particle size of 80 mesh into a V-mixer, mixing them therein for 60 minutes and extrusion molding the mixture. As for extrusion molding conditions, the extrusion molding was performed by molding the mixture for 8 seconds and by extruding it for 3 seconds, using a molding machine with a power capacity of 15 Tons (125 kg/cm$^2$) at a temperature of 120□. Further, each of the pellets was molded to have a depression extending from the center of a bottom surface of the pellet toward the interior of the pellet when molding the pellet. The diameter and height of a lowermost end of the depression were about 3 mm, respectively. The top and bottom surfaces of the pellet were smoothly curved in the form of a dome.

Raw material powder adhering to an outer surface of each of the pellets produced as such was blown away by air so that the pellet could be cleaned. Then, the pellet was immersed in 10% PMMA solution with a toluene solvent for 6 hours to be coated. Thereafter, the pellet was taken out from the solution, the remaining coating solution on the pellet was blown away by air, and the pellet was dried for 8 hours in a low temperature dryer at a temperature of 75☐. The dried pellet was wrapped with a shrinkable film made of PVC material. The shrinkable film was closely attached to the pellet to cover the side surface and edges of the top and bottom surfaces of the pellet.

After the wrapping of the shrinkable film, the pellet was immersed in 10% PS solution for 1 hour to be coated again. After this coating, the remaining coating solution on the pellet was blown away by air as described above, and the pellet was then dried in the same oven for 2 hours.

After the coating, a hole was drilled from the top of the pellet using a 2 mm drill bit so that it communicated with the depression formed when the molding the pellet and thus a hole was formed at the center of the pellet. After forming the hole, powder adhering to the outer surface of the pellet was blown away by air to be cleaned. Then, the pellet was immersed again in the 10% PS solution with the toluene solvent for 5 minutes to be coated. After this coating, air was caused to blow toward the pellet so that the coating solution did not remain in the hole, and the pellet was dried in the low temperature dryer for 1 hour.

Then, 50% PVA solution with the toluene solvent was sprayed onto the top and bottom of the dried pellet by using a spray to be coated. After the coating, the pellet was dried in the low temperature dryer described above for 2 hours. The spray coating and drying steps were further performed once more. Finally, the pellet-type formulation was prepared.

Example 2

Preparation of Pellet-Type Formulation 3000 g of light ash and 3000 g of heavy ash with 99.2% or more purity for food additives and 180 g of gelatin with the particle size of 80 mesh were charged into and mixed in the V-mixer for 60 minutes. Then, 180 ml of 10% PMMA resin solution with toluene solvent was added thereto. The mixture was further mixed again for 1 hour by using the V-mixer. After completion of the mixing, the mixture was put at room temperature for about 1 hour so that it could be dried and the solvent could be volatilized, and then, it was further mixed in the V-mixer for 10 minutes.

Pellets in the form of a cylinder with a diameter of about 20 mm and a height of about 5 mm were produced by extrusion molding the mixture under the same conditions as Example 1.

The raw material powder adhering to the outer surface of each of the pellets produced as such was blown away by air so that the pellet could be cleaned. Then, the pellet was immersed in 10% PVAC solution with the toluene solvent for 1 hour to be coated. Thereafter, the pellet was taken out from the solution and dried for 30 minutes in the low temperature dryer at the temperature of 75☐. The dried pellet was wrapped with the shrinkable film made of PVC material. The shrinkable film was closely attached to the pellet to cover the side surface and the edges of the top and bottom surfaces of the pellet.

After the wrapping of the shrinkable film, the pellet was put into a jig and spray coated with 50% PS solution. The coated pellet was then dried in the same low temperature dryer for 12 hours.

The dried pellet was coated by spraying the 10% PVAC solution described above thereon. After this coating, the coated pellet was dried in the low temperature dryer for 1 hour. A hole was drilled from the top of the dried pellet using the 2 mm drill bit so that it can be formed through the pellet at the center thereof.

Examples 3 to 5

Preparation of Pellet-Type Formulation

Example 3

1000 g of light ash with 99.2% or more purity for food additives and 200 g of PMMA powder were first mixed in the V-mixer for 30 minutes. 1000 g of heavy ash with 99.2% or more purity for food additives and 60 g of gelatin with the particle size of 80 mesh were added thereto and mixed with one another for 60 minutes.

Pellets in the form of a cylinder with a diameter of about 20 mm and a height of about 9.6 to 9.8 mm were produced by extrusion molding the mixture under the same conditions as Example 1. Each of the pellets was produced such that a conical depression with a height of 6 mm extending from the center of the bottom surface of the pellet was formed therein. A lower diameter of the depression was about 5 mm and the weight of the produced pellet was between 4.5 to 4.8 g. The pellet was put at a temperature of 230☐ to which room temperature was increased by using a high temperature dryer, for 30 minutes. Then, the pellet was immersed in the same PVAC solution as Example 2 for 5 minutes so that it can be primarily coated. The coated pellet was put in the low temperature dryer at the temperature of 75☐ and completely dried for 20 minutes. The side surface of the dried pellet was completely wrapped with the shrinkable film.

The pellet wrapped with the shrinkable film was put into the jig and spray coated with 50% PVAC solution with toluene solvent. The coated pellet was then dried in the same low temperature dryer for 10 hours. The dried pellet was spray coated again with the 50% PVAC solution and dried in the low temperature dryer for 1 hour.

The dried pellet was drilled from a side opposite to the side where the depression was formed by using drill bits with diameters of 2 mm and 2.5 mm, so that the hole was formed through the pellet at the center thereof.

Example 4

1200 g of light ash with 99.2% or more purity for food additives and 200 g of PMMA powder were first mixed in the V-mixer for 30 minutes. 1200 g of heavy ash with 99.2% or more purity for food additives and 60 g of gelatin with the particle size of 80 mesh were added thereto and mixed with one another for 60 minutes.

Pellets in the form of a cylinder with a diameter of about 20 mm and a height of about 9.6 to 9.8 mm were produced by extrusion molding the mixture under the same conditions as Example 1. Each of the pellets was produced such that the conical depression with a height of 6 mm extending from the center of the bottom surface of the pellet was formed therein.

The lower diameter of the depression was about 5 mm and the weight of the produced pellet was between 4.5 to 4.8 g. The pellet was put at a temperature of 230☐ to which room temperature was increased by using the high temperature dryer, for 30 minutes. Then, the pellet was immersed in the same PVAC solution as Example 2 for 5 minutes so that it can be primarily coated. The coated pellet was put in the low temperature dryer at the temperature of 60☐ and completely dried for 30 minutes. The side surface of the dried pellet was completely wrapped with the shrinkable film.

The pellet wrapped with the shrinkable film was put into the jig and spray coated with 50% PVAC solution with toluene solvent. The coated pellet was then dried in the same low temperature dryer for 10 hours. The dried pellet was spray coated again with the 50% PVAC solution and dried in the same low temperature dryer for 1 hour.

The dried pellet was drilled from the side opposite to the side where the depression was formed by using the drill bit with a diameter of 2.5 mm, so that the hole was formed through the pellet at the center thereof.

Example 5

1500 g of light ash with 99.2% or more purity for food additives and 200 g of PMMA powder were first mixed in the V-mixer for 30 minutes. 1500 g of heavy ash with 99.2% or more purity for food additives and 60 g of gelatin with the particle size of 80 mesh were added thereto and mixed with one another for 60 minutes.

Pellets in the form of a cylinder with a diameter of about 20 mm and a height of about 9.6 to 9.8 mm were produced by extrusion molding the mixture under the same conditions as Example 1. Each of the pellets was produced such that the conical depression with a height of 6 mm extending from the center of the bottom surface of the pellet was formed therein. The lower diameter of the depression was about 5 mm and the weight of the produced pellet was between 4.5 to 4.8 g. The pellet was put at a temperature of 230☐ to which room temperature was increased by using the high temperature dryer, for 30 minutes. Then, the pellet was immersed in the same PVAC solution as Example 2 for 5 minutes so that it could be primarily coated. The coated pellet was put in the low temperature dryer at the temperature of 60☐ and completely dried for 30 minutes. The side surface of the dried pellet was completely wrapped with the shrinkable film.

The pellet wrapped with the shrinkable film was put into the jig and spray coated with 50% PVAC solution with the toluene solvent. The coated pellet was then dried in the same low temperature dryer for 10 hours. The dried pellet was spray coated again with the 50% PVAC solution and dried in the low temperature dryer for 1 hour.

The dried pellet was drilled from the side opposite to the side where the depression was formed by using the drill bit with a diameter of 2.5 mm, so that the hole was formed through the pellet at the center thereof.

Example 6

Measurement Tests of Medicine Injection Rate Through Reaction Between the Pellet-Type Formulation Prepared in Examples 3 to 5 and Citric Acid Each of the pellets produced in Examples 3 to 5 was employed and caused to react with citric acid in an ANAPA® series medicine injection apparatus having a gas supply device capable of producing gas through a reaction with a liquid acid, which is manufactured and sold by E-WHA International Inc. (website: www.ewhainc.co.kr) located at 39-1 Seosomun-Dong, Jung-Gu, Seoul, Republic of Korea, such as disclosed in International Application No. PCT/KR00/01530 (International Publication No. WO 02/11791 A1). Then, amounts of physiological saline solution injected per unit time were measured according to production of $CO_2$ gas for at least 10 hours, respectively. Test results are shown in Table 1 below.

TABLE 1

|  | Example 3 | Example 4 | Example 5 | |
| --- | --- | --- | --- | --- |
| Height of depression of pellet | 6 mm | 6 mm | 6 mm | 6 mm |
| Diameter of upper hole portion of pellet | 2 mm | 2.5 mm | 2.5 mm | 2.5 mm |
| Product No. of ANAPA ® medicine injection apparatus used | AC0605 | AC1010 | AC1020 | AC1100 |
| Amount of medicine injected per unit time | 0.5 ml/hr | 1.0 ml/hr | 2.0 ml/hr | 10.0 ml/hr |

As can be seen from the above table, when each of the pellets was caused to react with the acid, a constant amount of gas per unit time was continuously produced for a certain period of time. Thus, they could be usefully employed in an apparatus for injecting medicine at a constant rate. Further, as shown in the table, it can be understood that the amount of gas produced per unit time, i.e. the injection amount of liquid, can be controlled by adjusting the size of the hole formed in the pellet as well as the composition ratios of the components constituting the pellet.

The pellet-type formulation prepared as such can continuously produce a constant amount of $CO_2$ gas per unit time for a predetermined period of time when reacting with the liquid acid. Therefore, the pellet-type formulation can be effectively used in a portable liquid supply apparatus or the like for continuously injecting medicine into a patient at a constant rate for a predetermined period of time.

Further, in addition to such a field, the pellet-type formulation can be easily used in a field requiring the production of gas such as $CO_2$ at a constant rate for a predetermined period of time.

Moreover, in the pellet-type formulation, an amount of gas produced per unit time, a period of time for continuous production of gas, or the like can be easily modified and changed by changing the ratios among the components constituting the pellet or adjusting the size and shape of the pellet itself, the size of the hole, or the like.

It should be understood that the detailed constitution and preferred examples of the present invention described above do not limit the present invention and those skilled in the art can easily change and modify the present invention by using techniques known in the art. Such changes and modifications fall within the scope of the invention as far as they do not depart from the constitution and fundamental spirit defined by the appended claims.

What is claimed is:
1. A gas generating device, comprising:
  a body formed from a composition comprising a chemical compound which is capable of generating a gas from a reaction of the composition with an activating compound;
  a coating of a material on the body, the material being substantially resistant to the activating compound; and at least one exposed area of the body that is not covered by the coating,
wherein the composition comprises from about 87 wt % to about 92 wt % of the chemical compound, from about 5% to about 10% of polymethyl methacrylate resin, and from about 1.5% to about 3% of gelatin.

2. The device of claim 1, wherein the exposed area is substantially smaller than the total surface area of the body.

3. The device of claim 1, wherein prior to the reaction with the activating compound, the exposed area is less than about 20% of the total surface area of the body.

4. The device of claim 1, wherein the body has a substantially cylindrical aperture, wherein the at least one exposed area is located on a surface of the substantially cylindrical aperture.

5. The device of claim 1, wherein the body is substantially cylindrical and has a substantially cylindrical hollow, and wherein the at least one exposed area is located on a surface of the substantially cylindrical hollow.

6. The device of claim 1, wherein the body is pellet-shaped, and wherein the at least one exposed area is located at about an end of the pellet-shaped body.

7. The device of claim 1, wherein the chemical compound is selected from the group consisting of metal carbonates and metal hydrogen carbonates.

8. The device of claim 7, wherein the metal carbonates comprise sodium carbonate, potassium carbonate, calcium carbonate and magnesium carbonate, and wherein the metal hydrogen carbonates comprise sodium hydrogen carbonate and potassium hydrogen carbonate.

9. The device of claim 1, wherein the activating compound is selected from the group consisting of tartaric acid, citric acid, acetic acid, oxalic acid, lactic acid, succinic acid, malic acid, maleic acid, fumaric acid, hydrochloric acid and sulfuric acid.

10. A method of making the device of claim 1, comprising:
providing a composition comprising from about 87 wt % to about 92 wt % of a chemical compound that is capable of generating a gas from a reaction of the composition with an activating compound, from about 5% to about 10% of PMMA resin, and from about 1.5% to about 3% of gelatin;
forming the composition into a shaped body;
coating the shaped body of the composition with a material substantially resistant to the activating compound; and
forming the at least one exposed area.

11. The method of claim 10, further comprising designing shape, size and location of the at least one exposed area so as to accomplish a controlled generation of the gas for an extended period of time upon contacting the device with the activating compound.

12. The method of claim 11, wherein the extended period of time is from about 3 minutes to about 24 hours.

13. A method of generating a gas, comprising:
providing the device of claim 1;
contacting the device with the activating compound; and
allowing the activating compound to contact the at least one exposed area of the device and to react with the chemical compound of the composition, thereby generating the gas.

14. A method of moving a piston, comprising:
contacting the activating compound with the chemical compound through the at least one exposed area of the device of claim 1, thereby generating a gas;
collecting the generated gas in an enclosed space, the gas having a pressure within the enclosed space; and
moving a piston with the pressure of the gas.

15. A method of supplying a liquid, comprising:
providing a liquid contained in a container having an outlet;
providing the device of claim 1 and the activating compound;
contacting the activating compound with the chemical compound through the at least one exposed area of the device, thereby generating a gas;
collecting the generated gas in an enclosed space, the gas having a pressure within the enclosed space;
forcing the liquid contained in the container with the pressure of the gas, thereby discharging the liquid from the container through the outlet;
supplying the discharged liquid to a person or object in need of such supply.

16. The method of claim 15, wherein contacting the activating compound with the chemical compound is continued for an extended period of time.

17. The method of claim 15, wherein supplying the discharged liquid is continued for an extended period of time.

* * * * *